United States Patent
Nowottny et al.

(10) Patent No.: US 11,229,587 B2
(45) Date of Patent: *Jan. 25, 2022

(54) HYDROGEN PEROXIDE FORMULATIONS IN BARRIER LAYER FILMS WITH A METALLIZED LAYER

(71) Applicant: Henkel AG & Co. KGaA, Duesseldorf (DE)

(72) Inventors: Marc Nowottny, Moenchengladbach (DE); Torsten Lechner, Langenfeld (DE); Wolfgang Barthel, Langenfeld (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/758,618

(22) PCT Filed: Oct. 31, 2018

(86) PCT No.: PCT/EP2018/079786
§ 371 (c)(1),
(2) Date: Apr. 23, 2020

(87) PCT Pub. No.: WO2019/120725
PCT Pub. Date: Jun. 27, 2019

(65) Prior Publication Data
US 2021/0177713 A1    Jun. 17, 2021

(30) Foreign Application Priority Data

Dec. 18, 2017   (DE) ..................... 10 2017 223 029.0

(51) Int. Cl.
| | | |
|---|---|---|
| *A61Q 5/08* | (2006.01) |
| *A61K 8/22* | (2006.01) |
| *A61K 8/34* | (2006.01) |
| *A61K 8/46* | (2006.01) |
| *A61Q 5/10* | (2006.01) |
| *B32B 7/12* | (2006.01) |
| *B32B 27/08* | (2006.01) |
| *B32B 27/32* | (2006.01) |
| *B32B 27/36* | (2006.01) |

(52) U.S. Cl.
CPC ............... *A61K 8/22* (2013.01); *A61K 8/342* (2013.01); *A61K 8/463* (2013.01); *A61Q 5/08* (2013.01); *A61Q 5/10* (2013.01); *B32B 7/12* (2013.01); *B32B 27/08* (2013.01); *B32B 27/32* (2013.01); *B32B 27/36* (2013.01); *A61K 2800/4324* (2013.01); *A61K 2800/596* (2013.01); *A61K 2800/87* (2013.01); *B32B 2250/03* (2013.01); *B32B 2250/24* (2013.01); *B32B 2255/10* (2013.01); *B32B 2255/205* (2013.01); *B32B 2307/518* (2013.01); *B32B 2307/7244* (2013.01); *B32B 2307/7246* (2013.01); *B32B 2307/732* (2013.01); *B32B 2307/748* (2013.01); *B32B 2439/46* (2013.01)

(58) Field of Classification Search
CPC .......... A61Q 5/08; A61K 8/342; A61K 8/463; A61K 2800/5422; A61K 2800/5424; A61K 2800/4324; A61K 2800/87; B32B 2250/03; B32B 2250/24; B32B 2250/10; B32B 2255/205; B32B 2307/518; B32B 2307/7244; B32B 2307/7246; B32B 2307/732; B32B 2307/748; B32B 2439/46
USPC .......................................................... 424/62
See application file for complete search history.

(56) References Cited

U.S. PATENT DOCUMENTS

| | | | |
|---|---|---|---|
| 6,503,634 B1 | 1/2003 | Utz et al. | |
| 2006/0128915 A1* | 6/2006 | Nagai ..................... | C07C 41/06 526/247 |
| 2011/0232669 A1* | 9/2011 | Suenger ................... | A61K 8/44 132/208 |
| 2017/0150800 A1* | 6/2017 | Mueller ................. | A61K 8/368 |
| 2017/0266086 A1 | 9/2017 | Lechner et al. | |
| 2017/0340553 A1 | 11/2017 | Anderheggen et al. | |
| 2019/0217583 A1 | 7/2019 | Nowottny et al. | |

FOREIGN PATENT DOCUMENTS

| | | |
|---|---|---|
| DE | 102014224804 A1 | 6/2016 |
| DE | 102015223838 A1 | 6/2017 |
| DE | 102016209464 A1 | 11/2017 |
| EP | 0792846 A1 | 9/1997 |
| EP | 1036813 A1 | 9/2000 |
| EP | 1541340 A1 | 6/2005 |
| EP | 2371539 A1 | 10/2011 |
| WO | 2018046158 A1 | 3/2018 |

OTHER PUBLICATIONS

EPO, International Search Report issued in International Application No. PCT /EP2018/079786, dated Feb. 11, 2019.

* cited by examiner

*Primary Examiner* — Eisa B Elhilo
(74) *Attorney, Agent, or Firm* — Lorenz & Kopf, LLP

(57) ABSTRACT

The present disclosure concerns a cosmetic product for modifying the natural color of keratinous fibers, in particular human hair, comprising at least one packaging (VP) and a cosmetic composition (KM) contained in this packaging (VP). The packaging is made of a multi-layer film (F) comprising at least two polymer layers (P1) and (P2) and at least one barrier layer (BS). The cosmetic composition comprises at least one oxidizing agent, at least one $C_8$-$C_{30}$ alcohol, at least one anionic surfactant and at least one non-ionic surfactant. The use of the packaging (VP) in combination with the cosmetic composition (KM) does surprisingly not lead to a swelling of the packaging or excessive water loss of the composition (KM) during storage.

20 Claims, No Drawings

HYDROGEN PEROXIDE FORMULATIONS IN BARRIER LAYER FILMS WITH A METALLIZED LAYER

CROSS-REFERENCE TO RELATED APPLICATION

This application is a U.S. National-Stage entry under 35 U.S.C. § 371 based on International Application No. PCT/EP2018/079786, filed Oct. 31, 2018, which was published under PCT Article 21(2) and which claims priority to German Application No. 10 2017 223 029.0, filed Dec. 18, 2017, which are all hereby incorporated in their entirety by reference.

TECHNICAL FIELD

The present disclosure is in the field of cosmetics and relates to a product for oxidative color change of keratinous fibers, in particular human hair, comprising an oxidant-containing composition packaged in a packaging. The oxidant-containing composition comprises at least one $C_8$-$C_{30}$ alcohol, at least one non-ionic surfactant and at least one anionic surfactant. The packaging is manufactured from a special multi-layer film composite system, the wall of which comprises at least two polymeric layers and a barrier layer. The barrier layer has a permeation barrier effect for gases and water vapor. The barrier layer comprises a metal.

BACKGROUND

Changing the color of keratinous fibers, especially hair, is an important area of modern cosmetics. The appearance of the hair may be adapted to current fashion trends as well as to the individual wishes of each person. The expert knows various methods for changing the color of hair. The hair color may be changed temporarily by using direct dyes. In this process, already formed dyes diffuse from the dye into the hair fiber. Dyeing with direct dyes is associated with a low level of hair damage, but a disadvantage is the low durability and the fast washability of the colorations obtained with direct dyes.

If the consumer desires a long-lasting color result or a color shade that is lighter than the original hair color, oxidative color modifiers are usually used. For permanent, intensive colorations with corresponding fastness properties, so-called oxidative colorants are used. Such dyes usually contain oxidative colorant precursors, so-called developer components and coupler components, which form the actual dyes under the influence of oxidants—usually hydrogen peroxides. Oxidative colorants are exemplified by excellent, long-lasting dyeing results.

Oxidative color modifiers are usually marketed in the form of two-component agents, in which two different compositions are separately packaged in two separate packagings and are not mixed together until shortly before use. The first composition is a formulation—usually acidic for stability reasons—which contains, for example, hydrogen peroxide in concentrations of from about 1.5 to about 12% by weight as an oxidizing agent. The oxidizing agent formulation is usually in the form of an emulsion or dispersion and is usually provided in a plastic bottle with a resealable outlet opening (developer bottle).

This oxidizing agent formulation is mixed with a second composition before use. This second composition is an alkaline formulation which is often in the form of a cream or a gel and which, if a color change is desired at the same time as the brightening, also contains at least one oxidative colorant precursor. This second composition may, for example, be provided in the form of a tube or in the form of a plastic or glass container.

In the usual application form described above, the second composition, which contains the alkalizing agent and/or the oxidative colorant precursors, is transferred from the tube or container into the developer bottle and then mixed by shaking with the hydrogen peroxide composition already in the developer bottle. In this way, the application mixture is prepared in the developer bottle. Application to the hair is then carried out via a small spout or outlet opening at the top of the developer bottle. The spout or outlet opening is opened after shaking and the application mixture may be removed by pressing the flexible developer bottle.

The use of the developer bottle requires a certain routine from the user, so that some users prefer to prepare the application mixture in a mixing bowl and apply it with a brush.

When preparing the application mixture in a bowl, both components—the first composition containing the oxidizing agent and the second composition containing an alkalizing agent and/or oxidative colorant precursors—are completely transferred into a bowl or similar vessel and stirred there, for example with the aid of a brush. The application mixture is then removed from the mixing bowl using the brush. With this form of application, the use of a voluminous and expensive developer bottle is not necessary, and the search continues for inexpensive and material-saving packaging forms for the oxidizing agent composition.

In this context, packaging in pocket or bag form, which is usually made of plastic films or metal foils, is an inexpensive form of packaging with low material consumption.

Such packaging may be produced, for example, by gluing or hot pressing two plastic foils lying one on top of the other, with the gluing taking place on all edges of the foils. The interior of the packaging (i.e. the plastic bag) created by the bonding may then be filled with the desired cosmetic composition. The packaging may be opened by tearing or cutting open the plastic bag.

However, filling oxidizing agent compositions into such packaging is associated with problems caused by the reactivity of the oxidizing agent. Oxidizing agents are highly reactive substances which—depending on the storage conditions and the presence of decomposing impurities—decompose in small amounts and produce oxygen (i.e. gas).

The developer bottles known from the state of the art are usually only filled with the oxidizing agent composition to a maximum of half, usually only to a third of their internal volume. As a rule, developer bottles are made of polyethylene. Since polyethylene is permeable to both water vapor and other gases, there is no or only very slight excess pressure in the developer bottle. In addition, developer bottles are usually provided with strong, thick walls and a sturdy screw cap, so that the diffusion of water vapor or gases through the thickness of the walls is reduced and a slight increase in pressure within the bottle has no negative effects.

In contrast, bag-shaped packaging is usually completely filled with the liquid composition, and there is practically no excess air space in the filled bag. In addition, such packaging should be flexible, and when opened (e.g. torn open or cut open) there should be no uncontrolled escape of the composition. For this reason, when packaging liquid compositions, the creation of excess pressure in the package should be avoided if possible.

If an oxidizing agent composition is in such packaging, the gas (oxygen) produced during storage may cause the package to expand. Since the edges of the package are usually only glued together, in the worst case, strong inflation may lead to bursting of the packaging. For these reasons, when storing oxidizing agent-containing compositions, the choice of the film material of which the packaging is made is of great importance.

Packaging made of pure plastic such as polyethylene or polypropylene is permeable to both water vapor and gases. When storing a composition containing oxidizing agents in polyethylene or polypropylene packaging, the packaging does not expand. Due to the high permeability of the comparatively thin film of the packaging to water vapor, however, the water content of the composition is reduced. If the composition is stored in the packaging for several weeks or months, the water loss exceeds the maximum value permitted for adequate storage stability.

The production of suitable packaging for formulations containing hydrogen peroxide is a challenge. The above mentioned properties for the permeability of oxygen and water vapor have to be adjusted in such a way that a sufficient storage stability is given. The layer thickness of the film should be kept as low as possible for environmental reasons and to preserve resources. Furthermore, the layer thickness naturally also has an influence on the manufacturing costs. Against this background, thin layers are desired, but these do not always guarantee sufficient mechanical strength. If different materials are combined in a multi-layer film in order to satisfy a wide range of requirements, the manufactureability of the multi-layer film must also be guaranteed. Certain materials cannot be combined with each other because the cohesion between layers is not always sufficient or because their processing temperatures may be so different that joint processing is difficult.

Finally, the film materials are of great importance, especially when storing a multi-component system, as substances from the multi-component system can diffuse into the films and promote the detachment of layers forming the film. The choice of components of a hydrogen peroxide-containing formulation therefore also has an impact on the choice of packaging.

BRIEF SUMMARY

The objective of the present application was to package hydrogen peroxide-containing formulations in such a way that the mechanical strength of the packaging is sufficiently high to allow safe storage, but that easy access to the ingredients is guaranteed.

Surprisingly, it has now been found that oxidizing agent-containing compositions may be packaged where the water vapor permeability is low and inflation may be reduced by allowing the film to have a certain level of oxygen permeability. The films include a special film composite system and also have a barrier layer. By reducing the water vapor permeability, but adjusting the oxygen permeability to a sufficiently high level, the tendency to expand due to oxygen, which is formed from the hydrogen peroxide, is reduced and the mechanical strength is increased over time.

Cosmetic products for modifying the color of keratinous fibers are provided. In an exemplary embodiment, the cosmetic product includes a packaging comprising a multi-layer film. The multi-layer film includes a first polymer layer, a second polymer layer, and a barrier layer. The first polymer layer is formed of polyethylene terephthalate or polyethylene naphthalate, the second polymer layer is formed of a polyolefin, and the barrier layer is formed of metallized oriented polypropylene. A cosmetic composition is packaged in the packagin and comprises an oxidizing compound, a $C_8$-$C_{30}$ alcohol, an anionic surfactant, and a non-ionic surfactant.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The subject-matter of the present disclosure is a cosmetic product for modifying the natural color of keratinous fibers, in particular human hair, comprising
(i) at least one packaging (VP) comprising at least one multi-layer film (F) comprising at least one first polymer layer (P1), at least one second polymer layer (P2) and at least one barrier layer (BS), and
(ii) at least one cosmetic composition (KM) packaged in the packaging (VP) and containing:
a) at least one oxidizing compound,
b) at least one $C_8$-$C_{30}$ alcohol,
c) at least one anionic surfactant, and
d) at least one non-ionic surfactant,
wherein the first polymer layer (P1) is formed of polyethylene terephthalate or polyethylene naphthalate, in particular polyethylene terephthalate, the second polymer layer (P2) is formed of a polyolefin, in particular polyethylene, and the barrier layer (BS) is formed of metallized, oriented polypropylene.

Keratinous fibers, keratin-containing fibers or keratin fibers are furs, wool, feathers and in particular human hair. Although the products as contemplated herein are primarily suitable for lightening and dyeing keratinous fibers, there is nothing in principle to prevent their use in other areas.

The product as contemplated herein is a product for the oxidative color change of keratinous fibers, i.e. a product which is applied on the human head in order to achieve an oxidative coloring, a lightening, a bleaching or a color nuance of the hair. In this context, color nuance is understood to be a coloring in which the color result is lighter than the original hair color. That the product is to be used "to change the natural color" means that the product either comprises only an oxidizing agent for bleaching, or that the product comprises an oxidizing agent used with a coupler that is not part of the present disclosure to achieve a color change, or that the product is used with a dye that is not part of the present disclosure for further hair coloring.

Furthermore, the term "packaging" is understood to mean, as contemplated herein, a packaging which is preferably in the form of a sachet. A sachet is a small package in the form of a bag or pouch, which is often used in the packaging of cosmetics. The capacity of the packaging, in particular of the sachet, may, for example, be from about 5 to about 1000 ml, preferably from about 10 to about 200 ml and particularly preferably from about 20 to about 50 ml.

In addition, a multi-layer film (F) in the context of the present disclosure is understood to be a thin, flat and windable strip including the at least one polymer layer (P1) and the at least one polymer layer (P2). This multi-layer film (F) forms the wall of the packaging (VP). The packaging also contains a barrier layer (BS), which selectively permits or reduces the passage of water vapor and other gases such as oxygen.

The cosmetic product as contemplated herein comprises as a first component a packaging (VP) comprising at least one multi-layer film (F). This film comprises at least one first polymer layer (P1), at least one second polymer layer (P2) and at least one barrier layer (BS). This multi-layer film forms the wall or outer shell of the package. As described above, such packaging is usually made by gluing, pressing or welding two pieces of film on top of each other (the packaging (VP) is filled with the cosmetic composition (KM) at the same time), i.e. such packaging is closed at all edges. This package can be opened, for example, by tearing or cutting it open.

The thickness of the multi-layer film (F) determines the mechanical properties and the strength of the films. It should be designed in such a way that there is sufficient mechanical stability, but at the same time the film (F)—and thus the packaging (VP) produced from the film—should be flexible enough to allow complete removal of the cosmetic composition (KM) from the opened packaging (VP) by pressing or squeezing. A film meets these requirements if the film (F) has a certain total thickness. Preferred embodiments of the present disclosure are exemplified in that the at least one multi-layer film has a total thickness of from about 28 µm to about 220 µm, preferably of from about 52 µm to about 180 µm, more preferably of from about 80 µm to about 140 µm. For the purposes of the present disclosure, the total thickness of the film (F) is understood to be the sum of the thicknesses of all individual layers of the film (F).

The configuration of the layers (P1), (P2) and (BS) within the multi-layer film (F) may be different. Furthermore, it is also possible that the film (F) includes other layers in addition to the layers mentioned above. In addition, as contemplated herein, it is advantageous if all the previously mentioned layers are oriented parallel to the surfaces of the film (F), i.e. all layers have the same orientation. If the multi-layer film (F) contains the three layers (P1), (P2) and (BS) described above, the following layouts of the layers would be possible (viewed from the interior (in contact with the cosmetic composition (KM)) to the exterior):

a) *Interior*-Layer (P1)-Layer (P2)-Barrier layer (BS)-*Exterior*,
b) *Interior*-Layer (P1)-Barrier layer (BS)-Layer (P2)-*Exterior*,
c) *Interior*-Layer (P2)-Layer (P1)-Barrier layer (BS)-*Exterior*,
d) *Interior*-Layer (P2)-Barrier layer (BS)-Layer (P1)-*Exterior*,
e) *Interior*-Barrier layer (BS)-Layer (P1)-Layer (P2)-*Exterior*,
f) *Interior*-Barrier layer (BS)-Layer (P2)-Layer (P1)-*Exterior*.

However, as contemplated herein, it is preferred when the barrier layer (BS) is located between the first polymer layer (P1) and the second polymer layer (P2), the second polymer layer (P2) being located on the exterior of the package. In this case, the multi-layer film (F) is composed of three layers, the layer (P1) being at the innermost and in contact with the cosmetic composition (KM). The layer (P1) is in contact with the barrier layer (BS), and the barrier layer (BS) is in contact with the layer (P2). In this layer, the layers (P1) and (P2) are not adjacent to each other but are separated by the barrier layer (BS). The particular advantage of this configuration is that the—often very thin—barrier layer (BS) is not located on either the inner or outer surface of the multi-layer film (F), but is protected by the polymeric layer (P1) in the direction of the inside and by the polymeric layer (P2) in the direction of the outside. In this way, mechanical abrasion or mechanical destruction of the barrier layer (BS) can be avoided as far as possible. It is therefore advantageous in the context of the present disclosure if the at least one multi-layer film (F) contains the at least one barrier layer (BS) between the at least one first polymer layer (P1) and the at least one second polymer layer (P2). The use of such packaging has been shown to be particularly advantageous in terms of increased storage stability, as this layout avoids mechanical abrasion or mechanical destruction of the barrier layer (BS) as much as possible. In a further preferred embodiment, the barrier layer (BS) is also located between the two polymer layers P1 and P2, but the first polymer layer (P1) is located on the exterior of the package.

As contemplated herein, the exterior of the packaging (VP) is understood to be that side of the package which does not come into contact with the cosmetic composition (KM) but with the environment. The use of such packaging has proven to be particularly advantageous in terms of increased storage stability, as this arrangement shows neither swelling nor delamination during prolonged contact with an oxidizing agent-containing composition.

The first polymeric material of the first layer (P1) is, as contemplated herein, a polyester. This material may be a layer of one polymer type or a layer of a polymer blend. According to the present disclosure, the at least one first polymer layer (P1) is formed from polyethylene terephthalate or polyethylene naphthalate, in particular from polyethylene terephthalate. As contemplated herein, the term "formed" is understood to mean that the polymer layer contains at least about 70% by weight, preferably at least about 80% by weight, more preferably at least about 90% by weight, most preferably at least about 99% by weight, in each case based on the total weight of the polymer layer (P1), of the above-mentioned compounds.

Polyethylene terephthalate (PET) is a polymer from the polyester group. Polyethylene terephthalate may be produced, for example, by transesterification of dimethyl terephthalate with ethylene glycol at higher temperatures. In this transesterification reaction, methanol is split off, which is removed by distillation. The resulting bis(2-hydroxyethyl)-terephthalate is converted to PET by polycondensation, again producing ethylene glycol. Another method of producing polyethylene terephthalate is the direct polycondensation of ethylene glycol and terephthalic acid at high temperatures with distillation of the resulting water. Polyethylene terephthalate is exemplified by a particularly high mechanical strength. If the PET layer forms the outer layer, this also offers the advantage that the layers underneath may be printed without the print being rubbed off. The PET layer is transparent and provides a mechanical protective layer for the printed layer.

According to a preferred embodiment of the present disclosure, the layer thickness of the first polymer layer (P1) is from about 4 µm to about 50 µm, preferably from about 5 µm to about 35 µm, more preferably from about 6 µm to about 20 µm. The layer thickness of the PET layer used according to the preferred embodiment of the present disclosure is associated with special advantages, which are related to general properties of PET. PET is exemplified by high dimensional stability/stiffness. If PET with these layer thicknesses is chosen as the first polymer layer (P1), this offers an advantageous mechanical dimensional stability for the film. At the same time, the overall thickness of the film may be kept low, so that a material and resource-saving film may be provided.

Furthermore, the multi-layer film (F) from which the package is made comprises a second polymer layer (P2) of a second polymeric material. The second polymeric material can be a layer of one type of polymer or a layer of a polymer mixture. It is provided in the context of the present disclosure that the at least one second polymer layer (P2) is formed of a polyolefin, in particular of polyethylene. As contemplated herein, the term "formed" is understood to mean that the polymer layer contains at least about 70% by weight, preferably at least about 80% by weight, preferably at least about 90% by weight, in particular at least about 99% by weight, each relative to the total weight of the polymer layer (P2) of the aforementioned compounds.

The second polymeric material of the second layer (P2) of the multi-layer film (F) is a polyolefin, in particular polyethylene. Polyolefins are polymers which are produced from alkenes such as ethylene, propylene, 1-butene or isobutene by chain polymerization. Polyolefins are saturated hydrocarbons. They are semi-crystalline thermoplastics which are easy to process. They are exemplified by good chemical resistance. Polyethylene and polypropylene are widely used in film applications. As contemplated herein, polypropylene is therefore used for the second layer (P2), but polyethylene is preferred. Polyethylene is produced by polymerization of ethylene using various catalysts. For example, polyethylene can be produced by polymerizing ethylene in the gas phase or in suspension. The average relative molar mass may be controlled, for example, by adjusting a certain hydrogen partial pressure during the polymerization of ethylene. Polyethylene may be processed by extrusion and stretch blow molding, or by pressing, calendering, thermoforming and cold forming.

The second polymer layer (P2) serves as a supporting layer. Although polyethylene has the disadvantage of being permeable to oxygen and water vapor, it has the advantage of being inexpensive and, due to its low melting point—lower than that of polypropylene—it is easy and energy-saving to process.

According to a preferred embodiment of the present disclosure, the second polymer layer (P2) has a certain layer thickness. According to the preferred embodiment of the present disclosure, the second polymer layer (P2) has a layer thickness of from about 20 μm to about 150 μm, preferably of from about 30 μm to about 110 μm, more preferably of from about 40 μm to about 90 μm. In particular, the second polymer layer (P2) has a higher layer thickness than the first polymer layer (P1).

The polymer layers (P1) and (P2) of the multi-layer film (F) comprise organic polymeric materials, which generally have only an insufficient barrier effect against gases and water vapor. If the oxidizing agent-containing composition (KM) is packaged in a packaging (VP) made of a multi-layer film (F), which only comprises the two organic polymer layers (P1) and (P2), water vapor may escape unhindered, so that the water content in the composition (KM) changes in an unacceptable way during longer storage. To minimize the uncontrolled escape of water vapor from the packaging (VP), the organic polymer layers (P1) and (P2) are therefore used in combination with a barrier layer (BS).

The barrier layer (BS) has a passage barrier effect for gases and water vapor. As contemplated herein, this means that the barrier layer (BS) reduces and controls the permeation rate of water vapor and gases through the film. A film (F) as contemplated herein, which has a barrier layer (BS) in addition to the layers (P1) and (P2), thus has a reduced water vapor permeability and a reduced gas permeability compared to a comparable film (with the same overall thickness), which only has the two layers (P1) and (P2) but no barrier layer (BS).

For example, the barrier layer (BS) is a thin layer comprising an inorganic material, which may be applied to organic polymer layers using vacuum coating techniques (e.g. PVD "physical vapor deposition" or CVD "chemical vapor deposition").

If the barrier layer (BS) is a layer comprising at least one inorganic material, then the films may be made of metals, semi-metals or metal or semi-metal oxides, for example aluminum, aluminum oxides, magnesium, magnesium oxides, silicon, silicon oxides, titanium, titanium oxides, tin, tin oxides, zirconium, zirconium oxide and/or carbon.

As contemplated herein, the barrier layer (BS) is made of metallized, oriented polypropylene. Polypropylene is alternatively also known as poly(l-methylethylene), and is a thermoplastic polymer belonging to the group of polyolefins. Polypropylene is produced by polymerization of propylene (propene) using various catalysts. For example, polypropylene may be produced by stereospecific polymerization of propylene in the gas phase or in suspension according to Giulio Natta. Polypropylene as contemplated herein may be isotactic and thus highly crystalline, but also syndiotactic or amorphous. The average relative molar mass may be controlled, for example, by adjusting a certain hydrogen partial pressure during the polymerization of the propene. For example, polypropylene may have average relative molar masses of approx. 150,000 to about 1,500,000 g/mol. Polypropylene may be processed by extrusion and stretch blow molding, or by pressing, calendering, thermoforming and cold forming.

The term oriented polypropylene is understood by the expert to mean a polypropylene film which is stretched during production following an extrusion or calendering step, namely stretched in the direction of extrusion and/or stretched at about 90° to the direction of extrusion. The film is preferably stretched in both directions, i.e. films in which the barrier layer—or the entire film—is biaxially stretched, particularly preferably simultaneously biaxially. During the stretching step the polymeric material is oriented. This is particularly important for the properties of the film layer in the case of polypropylenes, since the orientation step determines the shape of the crystalline domains of the polymeric material and thus the physical properties of the film.

The polypropylene film is metallized. Possible metals are the above mentioned metals aluminum, magnesium, silicon, titanium, tin, and zirconium, especially aluminum. The metals are vapor-deposited onto the carrier film. According to a preferred embodiment of the present disclosure, the ratio of the layer thickness of metal to oriented polypropylene is from about 1:1000 to about 1:10, preferably from about 1:500 to about 1:50, more preferably from about 1:200 to about 1:100.

The production of films with barrier layers comprising inorganic material is known. Also, the multi-layer film (F) used in accordance with the present disclosure may be manufactured by a process which is used for the manufacture of known films with barrier layers in the state of the art, as described for example in the documents EP 1036813 A1, EP 2371539 A1 and EP 1541340 A1.

The barrier layer (BS) may additionally include a thin layer of inorganic-organic hybrid polymers. These polymers are known in the literature under the technical term ORMOCER polymers. A typical ORMOCER polymer may be produced, for example, by hydrolytic polycondensation of an organo-functional silane with an aluminum compound and possibly with an inorganic oxide component. Corresponding syntheses are disclosed in EP 0792846 B 1, which is referred to in full here. Inorganic-organic hybrid polymers (ORMOCER polymers) have both inorganic and organic network structures. The inorganic silicate network structure can be formed in the sol-gel process by controlled hydrolysis and condensation of alkoxysilanes. The silicate network may be specifically modified by including metal alkoxides in the sol-gel process. By polymerization of organo-functional groups, which are introduced into the material by the organoalkoxylanes, an additional organic network is built up. The ORMOCER polymers produced in this way may be applied to layers (P1) and/or (P2) using conventional application techniques (spraying, brushing, etc.).

The thicker the barrier layer (BS), the greater or stronger is the barrier effect against the passage of gases and water vapor. The thickness of the barrier layer (BS) may therefore be selected depending on the desired barrier effect. According to a preferred embodiment of the present disclosure, the at least one barrier layer (BS) has a layer thickness of from about 4 μm to about 25 μm, preferably of from about 5 μm to about 20 μm, more preferably of from about 6 μm to about 18 μm.

The material, structure and layer thicknesses determine the permeability values of the film. The multi-layer film (F) of the packaging of the cosmetic product as contemplated herein is exemplified by advantageous properties with regard to oxygen permeability and water vapor permeability. The multi-layer film exhibits an oxygen transmission rate (OTR) at 23° C. and 50% relative humidity of from about 0.1 to about 5 cc/m$^2$/d/bar, preferably from about 0.2 to about 3.5 cc/m$^2$/d/bar, more preferably from about 0.5 to about 2.5 cc/m$^2$/d/bar, and a water vapor transmission rate at 38° C. and 100% relative humidity of from about 0.1 to about 5 g/m$^2$d, preferably from about 0.2 to about 3.5 g/m$^2$d, more preferably from about 0.5 to about 2.5 g/m$^2$d.

As contemplated herein, the permeability values of the film (F) are advantageously adjusted. The film (F) thus imparts advantageous barrier properties to the package, especially with regard to the permeability for water vapor: Water Vapor Transmission Rate (WVTR) measured in the unit g/(m$^2$d) or g/(m$^2$24 h) measured according to the ASTM F 1249 method at 38° C. ambient temperature and 100% relative humidity, and for oxygen: Oxygen Transmission Rate (OTR) measured in cm$^3$/(m$^2$d bar) or cm$^3$/(m$^2$24 h), where cm$^3$ is equal to cc, at an atmospheric pressure of 1 bar measured according to ASTM D 3985 at 23° C. ambient temperature and 50% relative humidity.

In addition to the layers (P1), (P2) and (BS) described so far, the multi-layer film (F) may additionally comprise one or more further layers. These additional layers may, for example, be intermediate layers and/or adhesive layers. It is therefore preferred as contemplated herein if the at least one multi-layer film (F) additionally contains at least one further layer selected from the group of intermediate layers (SZ), adhesive layers (SK) and mixtures thereof.

For example, the films (F) may have further intermediate layers (SZ) to increase the mechanical stability. Intermediate layers may also prevent or minimize the permeation of polymers or remaining monomers from a polymer layer into the cosmetic composition (KM).

To increase bond strength, the films may also comprise one or more adhesive layers (SK) to reduce or prevent delamination (i.e. peeling or formation of an air space) between two layers.

A particularly preferred product as contemplated herein is exemplified in that the multi-layer film (F) comprises, in addition to the first polymer layer (P1), the second polymer layer (P2) and the barrier layer (BS), one or more further layers selected from intermediate layers (SZ) and/or adhesive layers (SK).

If the multi-layer film (F) contains other layers in addition to the layers (P1), (P2) and (BS), the following layouts of the layers are possible (from interior (in contact with the cosmetic composition (KM)) to exterior):

a) *Interior*-Layer (P1)-First adhesive layer (SK1)-Layer (P2)-Second adhesive layer (SK2)-Barrier layer (BS)-*Exterior*,
b) *Interior*-Layer (P1)-Adhesive layer (SK1)-Layer (P2)-Barrier layer (BS)-*Exterior*,
c) *Interior*-Layer (P1)-Layer (P2)-Second adhesive layer (SK2)-Barrier layer (BS)-*Exterior*,
d) *Interior*-Barrier layer (BS)-First adhesive layer (SK1)-Layer (P1)-Second adhesive layer (SK2)-Layer (P2)-*Exterior*,
e) *Interior*-Barrier layer (BS)-Adhesive layer (SK)-Layer (P1)-Layer (P2)-*Exterior*,
f) *Interior*-Barrier layer (BS)-Layer (51)-Adhesive layer (SK)-Layer (P2)-*Exterior*,
g) *Interior*-Layer (P1)-First adhesive layer (SK1)-Barrier layer (BS)-Second adhesive layer (SK2)-Layer (P2)-*Exterior*,
h) *Interior*-Layer (P1)-Adhesive layer (SK)-Barrier layer (BS)-Layer (P2)-*Exterior*,
i) *Interior*-Layer (P1)-Barrier Layer (BS)-Adhesive layer (SK)-Layer (P2)-*Exterior*

In any case, the film should be designed so that there is sufficient adhesion between the films. According to a preferred embodiment of the present disclosure, the bond strength of the film is from about 0.1 to about 10 N/15 mm, preferably from about 1 to about 8 N/15 mm, more preferably from about 1.5 to about 5 N/15 mm. This is measured by the ASTM F-904 method. The bond strength is a physical measure of the adhesive force between the layers. It is related to the two layers of a film with the lowest bond strength between two layers of the same film. The adhesive strengths set as contemplated herein result in a favorable mechanical stability over the storage time of the packaged cosmetic product.

Also, the strength between two bonded (sealed or sealed-off) films should be sufficient. According to a preferred embodiment of the present disclosure, the seal strength of the packaging (VP) is from about 10 to about 40 N/15 mm, preferably from about 15 to about 35 N/15 mm, more preferably from about 20 to about 30 N/15 mm, under the conditions of 150° C., 2.54 cm (1") and 4 kg/cm$^2$. The seal strength is measured according to ASTM F-88 under the above conditions. The challenge with packaging is always to ensure the mechanical durability of the packaging while at the same time making the contents easily accessible to the user. Adjusting the seal strength to these values enables both of these objectives to be achieved.

The term sealed seam refers to a seam by which the packaging is closed. Usually, two films are placed on top of each other for closing the packaging and are pressed together by a force perpendicular to the film surface. By heating the films in the area that is being compressed, parts of the compressed areas may fuse together, so that the films are welded together. There may also be an adhesive between the compressed films that strengthens the seam.

The product as contemplated herein comprises as a second component a cosmetic composition (KM) which is packaged in the packaging (VP) and which comprises at least an oxidizing agent, a $C_8$-$C_{30}$ alcohol, a non-ionic surfactant and an anionic surfactant.

The intended use of the product as contemplated herein is oxidative color change. For this purpose—as already described above—a cosmetic composition (KM) containing an oxidizing agent is usually mixed with a second composition (B) which is prepared separately from (KM). In this way, the ready-to-use oxidative color changing agent is produced. Depending on whether the oxidative color change is intended to achieve a bleaching, brightening or coloring effect, the composition (B) may contain different ingredients. If pure lightening or bleaching is to be achieved, composition (B) contains at least one alkalizing agent. If oxidative coloration is desired, the composition (B) often contains the oxidative colorant precursors in addition to the alkalizing agent. In order to ensure that the compositions (KM) and (B) may be mixed sufficiently quickly, both the composition (KM) and the composition (B) are usually free-flowing, aqueous or water-containing compositions.

As contemplated herein, the composition (KM) is an aqueous composition. The water content of the composition (KM) may, for example, be from about 60 to about 97% by weight, preferably from about 75 to about 93% by weight, more preferably from about 78 to about 91% by weight, in particular from about 80 to about 88.0% by weight, based on the total weight of the composition (KM). All weight data in % by weight refer to the total weight of water contained in the composition (KM), which is set in relation to the total weight of the composition (KM).

The cosmetic composition (KM) contains as first essential ingredient a) at least one oxidizing agent. Preference is given to certain oxidizing agents. It is therefore advantageous in the context of the present disclosure if the cosmetic composition (KM) contains at least one oxidizing compound selected from the group of persulfates, chlorites, hydrogen peroxides and attachment products of hydrogen peroxides to urea, melamine and sodium borate, in particular hydrogen peroxides. As contemplated herein, the use of hydrogen peroxide has proven to be particularly advantageous.

The concentration of the oxidizing agent in the composition (KM) is determined on the one hand by the legal requirements and on the other hand by the desired effect; preferably from about 0.5 to about 20.0% by weight solutions in water are used. Therefore, it is found to be preferred if the cosmetic composition (KM) contains at least one oxidizing compound, in particular hydrogen peroxide, in a total amount of from about 0.5 to about 20% by weight, preferably from about 1.0 to about 18% by weight, more preferably from about 1.2 to about 16% by weight, in particular from about 1.5 to about 15% by weight, based on the total weight of the cosmetic composition (KM). The higher the content of oxidizing agent, in particular hydrogen peroxide, in the composition (KM), the greater is the amount of gas produced by a proportional decomposition of the oxidizing agent. Compositions containing a higher concentration of oxidizing agent are therefore much more difficult to package in packaging (VP) than compositions containing a lower concentration. The amount of hydrogen peroxide refers to 100% hydrogen peroxide.

In the course of the work leading to this present disclosure, it was found that the product as contemplated herein is particularly suitable for the packaging and stable storage of higher concentrated hydrogen peroxide compositions (KM). Thus, packaging (VP) as contemplated herein, which contained compositions (KM) with from about 9 to about 12% by weight of hydrogen peroxide, showed no changes in volume (i.e. no swelling) and no unplanned openings (i.e. the packages did not burst open) even after storage at elevated temperature for several weeks.

The cosmetic composition (KM) contains as second essential ingredient b) at least one $C_8$-$C_{30}$ alcohol. In this context, mixtures of linear $C_{14}$-$C_{18}$ alcohols have proved particularly useful. Such mixtures in combination with the further features c) to d) of the composition (KM) lead to an excellent stabilization of the at least one oxidizing agent, especially of the hydrogen peroxide. It is therefore advantageous within the context of the present disclosure if the cosmetic composition (KM) contains at least one linear $C_{10}$-$C_{30}$ alcohol selected from the group of linear $C_{10}$-$C_{28}$ alcohols, linear $C_{12}$-$C_{26}$ alcohols, linear $C_{14}$-$C_{20}$ alcohols, linear $C_{14}$-$C_{18}$ alcohols as well as mixtures of the aforementioned alcohols, in particular a mixture of linear $C_{14}$-$C_{18}$ alcohols. In the context of the present disclosure, the mixture of cetyl alcohol and stearyl alcohol known as cetearyl alcohol, in particular a mixture of about 50% by weight cetyl alcohol and about 50% by weight stearyl alcohol, based on the total weight of the mixture, has proved to be particularly advantageous.

The at least one $C_5$-$C_{30}$ alcohol is preferably used in certain quantity ranges. Preferred embodiments of the present disclosure are exemplified in that the cosmetic composition (KM) contains the at least one linear $C_5$-$C_{30}$ alcohol, in particular a mixture of linear $C_{14}$-$C_{15}$ alcohols, in a total amount of from about 0.5 to about 8% by weight, preferably of from about 0.7 to about 7% by weight, more preferably of from about 1.0 to about 6% by weight, in particular of from about 1.5 to about 4% by weight, based on the total weight of the cosmetic composition (KM). The use of the total amounts of at least one $C_5$-$C_{30}$ alcohol, in particular the mixture of linear $C_{14}$-$C_{18}$ alcohols, as indicated above, in combination with the other ingredients of the cosmetic composition (KM) leads to a particularly good stabilization of the oxidizing agent contained in this composition, in particular the hydrogen peroxide.

As third essential ingredient c), the cosmetic composition (KM) contains at least one anionic surfactant. The use of these surfactants ensures sufficient miscibility of the cosmetic composition (KM) with composition (B) containing the oxidative colorant precursors and also ensures a high storage stability by avoiding precipitation of components of the cosmetic composition (KM). Preferred embodiments of the present disclosure are exemplified in that the cosmetic composition (KM) contains at least one anionic surfactant selected from the group of (i) $C_5$-$C_{18}$ alkyl ether sulfates with 1 to 10 moles of ethylene oxide per mole of $C_5$-$C_{15}$ alkyl ether sulfate, and salts thereof, in particular of sodium salts of $C_{12}$-$C_{14}$ alkyl ether sulfates with 2 mol ethylene oxide per mol $C_{12}$-$C_{14}$ alkyl ether sulfate, (ii) $C_5$-$C_{15}$ alkyl sulfates, (iii) salts of linear and branched $C_5$-$C_{30}$ carboxylic acids, (iv) acyl sarcosides having 8 to 24 carbon atoms in the acyl group, (v) acyl taurides having 8 to 24 carbon atoms in the acyl group, (vi) acyl isethionates having 8 to 24 carbon atoms in the acyl group, (vii) sulfosuccinic acid mono- and dialkyl esters with 8 to 24 carbon atoms in the alkyl group and sulfosuccinic acid mono-alkyl polyoxyethyl esters with 8 to 24 carbon atoms in the alkyl group and 1 to 6, preferably 1 to 4 oxyethyl groups, (viii) linear alpha-olefin sulfonates with 8 to 24 carbon atoms, (ix) alpha-sulfonic acid methyl esters of carboxylic acids with 8 to 30 carbon atoms, (x) alkyl and/or alkenyl ether phosphates, (xi) sulfonates of unsaturated carboxylic acids having 8 to 24 carbon atoms and 1 to 6 double bonds, (xii) $C_8$-$C_{30}$ ether carbonylates having 1 to 10 mol ethylene oxide per mol $C_5$-$C_{30}$ ether carboxylate and (xiii) mixtures thereof, in particular sodium salts of $C_{14}$-$C_{18}$ alkyl sulfates. An anionic surfactant particularly suitable within the scope of the present disclosure is the compound known under the INCI designation Sodium Cetearyl Sulfate (CAS No.: 59186-41-3).

In order to ensure a sufficient dispersion of all ingredients of the cosmetic product (KM), at least one anionic surfactant is preferably used in certain total quantities. It is therefore preferred in the context of the present disclosure if the cosmetic composition (KM) contains the at least one anionic surfactant, in particular sodium salts of $C_{14}$-$C_{15}$ alkyl sulfates, in a total amount of from about 0.1 to about 7% by weight, preferably of from about 0.1 to about 5.5% by weight, more preferably of from about 0.10 to about 4.0% by weight, in particular of from about 0.10 to about 3.5% by weight, based on the total weight of the cosmetic composition (KM).

As the fourth essential ingredient d), the cosmetic composition (KM) contains at least one non-ionic surfactant. The combination of at least one anionic surfactant and at least one non-ionic surfactant ensures excellent dispersion of the ingredients of the cosmetic composition (KM) and thus high storage stability. In addition, the use of such surfactant combinations leads to a good spreadability, in particular miscibility, of the cosmetic composition (KM) with the composition (B) containing the oxidative colorant precursors. It is therefore preferred in the context of the present disclosure if the cosmetic composition (KM) contains at least one non-ionic surfactant selected from the group including (i) ethoxylated and/or propoxylated alcohols and carboxylic acids having 8 to 30 carbon atoms and 2 to 30 ethylene oxide and/or propylene oxide units per mole of alcohol, (ii) attachment products of 30 to 50 moles of ethylene oxide to castor oil and hydrogenated castor oil, (iii) alkyl polyglucosides corresponding to the formula $R^1O$—$[G]_p$, in which $R^1$ is an alkyl and/or alkenyl radical containing 4 to 22 carbon atoms, G is a sugar unit containing 5 or 6 carbon atoms and p is a number of 1 to 10, (iv) monoethanolamides of carboxylic acids containing 8 to 30 carbon atoms and (v) mixtures thereof, more particularly attachment products of 40 mol ethylene oxide with hydrogenated castor oil. In the formula $R^1O$—$[G]_p$, the index number p indicates the degree of oligomerization (DP), i.e. the distribution of mono- and oligoglucosides, and represents a number between about 1 and about 10. Whereas p must always be an integer in a given compound and can assume the values p=1 to 6 in particular, the value p for a particular alkyl oligoglucoside is an analytically determined arithmetical quantity which is usually a fractional number. As contemplated herein, alkyl and/or alkenyl oligoglucosides with an average degree of oligomerization p of from about 1.1 to about 3.0 are preferably used. From the point of view of application technology, those alkyl and/or alkenyl oligoglucosides are preferred whose degree of oligomerization is less than about 1.7 and in particular lies between about 1.2 and about 1.7. The alkyl or alkenyl radical $R^1$ may be derived from primary alcohols containing 4 to 20, preferably 8 to 16 carbon atoms. As contemplated herein, alkyl oligoglucosides based on hardened $C_{12/14}$ coconut alcohol with a DP of from about 1-3, as they are commercially available under the INCI designation "Coco-Glucoside" for example, are particularly preferred. The non-ionic surfactants used with particular preference in the context of the present disclosure are ethoxylated alcohols with 14 to 18 carbon atoms and 20 to 30 moles of ethylene oxide units per mole of alcohol, in particular the compound known under the INCI designation Ceteareth-20 (CAS No.: 68439-49-6).

To ensure sufficient dispersion of all ingredients of the cosmetic product (KM), at least one non-ionic surfactant is preferably used in certain total quantities. Preferred embodiments of the present disclosure are exemplified in that the cosmetic composition (KM) contains the at least one non-ionic surfactant, in particular attachment products of 40 moles of ethylene oxide to hydrogenated castor oil, in a total amount of from about 0.10 to about 4.0% by weight, preferably of from about 0.12 to about 3.0% by weight, more preferably of from about 0.15 to about 2.5% by weight, in particular of from about 0.20 to about 2.0% by weight, based on the total weight of the cosmetic composition (KM).

Furthermore, the cosmetic composition (KM) may contain as a further ingredient e) at least one complexing compound. The use of this complexing compound leads to an improved stabilization of the oxidizing agent, in particular of the hydrogen peroxide, since the latter is protected against decomposition due to the reaction with metal ions of the cosmetic composition (KM). In the context of the present disclosure, certain complexing compounds are preferably used. As contemplated herein, it is therefore advantageous if the cosmetic composition (KM) contains at least one complexing compound selected from the group including β-alaninediacetic acid, cyclodextrin, diethylenetriaminepentamethylenephosphonic acid, ethylenediaminetetraacetic acid (EDTA) and their salts, etidronic acid, hydroxyethylethylenediaminetetraacetic acid (HEDTA) and its sodium salts, sodium salts of nitrilotriacetic acid (NTA), diethylenetriaminepentaacetic acid, phytic acid, hydroxypropylcyclodextrin, methylcyclodextrin, aminotrimethylenephosphonate-pentasodium, ethylenediaminetetramethylene phosphonate-pentasodium, diethylenetriamine-pentaacetate-pentasodium, pentasodium triphosphate, potassium EDTMP, sodium EDTMP, sodium dihydroxyethylglycinate, sodium phytate, sodium polydimethylglycinophenolsulfonate, tetrahydroxyethylethylenedi amine, tetrahydroxypropylethylenediamine, tetrapotassium etidronate, tetranatriumetidronate, tetrasodium iminodisuccinate, trisodium ethylenediamine disuccinate, tetrasodium N,N-bis(carboxymethyl)glutamate, tetrasodium DL-alanine-N,N-diacetate and desferrioxamine, in particular ethylenediamine tetraacetic acid. In the context of the present disclosure, the use of ethylenediaminetetraacetic acid (CAS No. xxxx) has proved to be particularly advantageous with respect to the stabilization of the oxidizing agent, in particular the hydrogen peroxide.

The at least one complexing compound, in particular ethylenediaminetetraacetic acid, is preferably present in cosmetic compositions (KM) in certain total amounts. This ensures adequate stabilization of the oxidizing agent, in particular the hydrogen peroxide. Preferred embodiments of the present disclosure are exemplified in that the cosmetic composition (KM) contains at least one complexing compound, in particular ethylenediaminetetraacetic acid, in a total amount of from about 0.10 to about 1.0% by weight, preferably from about 0.10 to about 0.80% by weight, more preferably from about 0.10 to about 0.60% by weight, in particular from about 0.10 to about 0.50% by weight, relative to the total weight of the cosmetic composition (KM).

In the course of the work leading to this present disclosure, it has been found that the use of the aforementioned essential ingredients b) to d) ensures that the cosmetic composition (KM) containing at least one oxidizing agent may be packaged and stored in the special packaging (VP) without this packaging—which has a barrier layer with a penetration barrier effect for gases and water vapour—swelling or bursting.

In this context, a very specific combination of the essential ingredients a) to d) of the cosmetic composition (KM)

has proven to be advantageous. In a preferred embodiment, the product as contemplated herein is exemplified in that the cosmetic composition (KM) contains hydrogen peroxide, a mixture of linear $C_{14}$-$C_{18}$ alcohols, a sodium salt of a $C_{16}$-$C_{18}$ alkysulfate and an addition product of 40 moles of ethylene oxide to hydrogenated castor oil, and ethylenediaminetetraacetic acid.

For further optimization of the storage stability, the above-mentioned compounds are preferably used in certain quantity ranges in composition (KM). Particularly preferred forms are exemplified by the fact that the cosmetic composition (KM) comprises a) from about 1.5 to about 15% by weight of hydrogen peroxide,
b) from about 1.0 to about 5.0% by weight of a mixture of linear $C_{14}$-$C_{15}$ alcohols,
c) from about 0.10 to about 3.5% by weight of a sodium salt of $C_{16}$-$C_{15}$ alkysulfates; and
d) from about 0.2 to about 2.0% by weight of an attachment product of 40 moles of ethylene oxide to hydrogenated castor oil.

The cosmetic composition (KM) preferably has an acidic pH value in order to avoid or reduce decomposition of the oxidizing agent used, in particular the hydrogen peroxide. It is therefore preferred in the context of the present disclosure that the cosmetic composition (KM) has a pH value (measured at 20° C.) of from about pH 1.5 to about pH 5.0, preferably of from about pH 2.0 to about pH 4.7, more preferably of from about pH 2.3 to about pH 4.4, in particular of from about pH 2.5 to about pH 4.

The composition (KM) contained in the packaging (VP) contains the essential ingredients in an aqueous or aqueous-alcoholic carrier, which may be a cream, an emulsion, a gel or a surfactant-containing foaming solution. In order to achieve the desired properties of these dosage forms, the composition (KM) may also contain additional active ingredients, auxiliary substances and additives.

The composition (KM) may also contain one or more acids to stabilize the oxidizing agent used, especially the hydrogen peroxide. It is therefore preferred in the context of the present disclosure if the cosmetic composition (KM) additionally contains at least one acid selected from the group of dipicolinic acid, citric acid, acetic acid, malic acid, lactic acid, tartaric acid, hydrochloric acid, phosphoric acid, pyrophosphoric acid and salts thereof, benzoic acid and salts thereof, 1-hydroxyethane-1,1-diphosphonic acid, ethylenediaminetetraacetic acid and salts thereof, sulfuric acid, and mixtures thereof, in particular a mixture of disodium pyrophosphate and benzoic acid and salts thereof.

A particularly high stabilization of the oxidizing agent, in particular of the hydrogen peroxide, is achieved if the above-mentioned acids are used in certain quantity ranges. It is therefore advantageous in this context if the at least one acid, in particular the mixture of disodium pyrophosphate and benzoic acid and their salts, is present in a total quantity of from about 0.1 to about 3.0% by weight, preferably of from about 0.5 to about 2.5% by weight, more preferably of from about 0.8 to about 2.0% by weight, in particular of from about 0.9 to about 1.5% by weight, based on the total weight of the cosmetic composition (KM).

The following tables show particularly preferred forms AF 1 to AF 28 of the cosmetic composition (KM) contained in the packaging (VP) (all figures in % by weight, unless indicated otherwise).

| | AF 1 | AF 2 | AF 3 | AF 4 |
|---|---|---|---|---|
| Oxidizing agent | 0.5-20 | 1.0-18 | 1.2-16 | 1.5-15 |
| $C_8$-$C_{30}$ alcohol | 0.50-7.0 | 0.50-6.5 | 1.0-6.0 | 1.0-5.0 |
| Anionic surfactant | 0.10-7.0 | 0.10-5.5 | 0.10-4.0 | 0.20-3.5 |
| Non-ionic surfactant | 0.10-4.0 | 0.12-3.0 | 0.15-2.5 | 0.20-2.0 |
| Cosmetic carrier [1] | ad 100 | ad 100 | ad 100 | ad 100 |

| | AF 5 | AF 6 | AF 7 | AF 8 |
|---|---|---|---|---|
| Oxidizing agent [2] | 0.5-20 | 1.0-18 | 1.2-16 | 1.5-15 |
| $C_8$-$C_{30}$ alcohol | 0.50-7.0 | 0.50-6.5 | 1.0-6.0 | 1.0-5.0 |
| Anionic surfactant | 0.10-7.0 | 0.10-5.5 | 0.10-4.0 | 0.20-3.5 |
| Non-ionic surfactant | 0.10-4.0 | 0.12-3.0 | 0.15-2.5 | 0.20-2.0 |
| Cosmetic carrier [1] | ad 100 | ad 100 | ad 100 | ad 100 |

| | AF 9 | AF 10 | AF 11 | AF 12 |
|---|---|---|---|---|
| Oxidizing agent [2] | 0.5-20 | 1.0-18 | 1.2-16 | 1.5-15 |
| $C_8$-$C_{30}$ alcohol [3] | 0.50-7.0 | 0.50-6.5 | 1.0-6.0 | 1.0-5.0 |
| Anionic surfactant | 0.10-7.0 | 0.10-5.5 | 0.10-4.0 | 0.20-3.5 |
| Non-ionic surfactant | 0.10-4.0 | 0.12-3.0 | 0.15-2.5 | 0.20-2.0 |
| Cosmetic carrier [1] | ad 100 | ad 100 | ad 100 | ad 100 |

| | AF 13 | AF 14 | AF 15 | AF 16 |
|---|---|---|---|---|
| Oxidizing agent [2] | 0.5-20 | 1.0-18 | 1.2-16 | 1.5-15 |
| $C_8$-$C_{30}$ alcohol [3] | 0.50-7.0 | 0.50-6.5 | 1.0-6.0 | 1.0-5.0 |
| Anionic surfactant [4] | 0.10-7.0 | 0.10-5.5 | 0.10-4.0 | 0.20-3.5 |
| Non-ionic surfactant | 0.10-4.0 | 0.12-3.0 | 0.15-2.5 | 0.20-2.0 |
| Cosmetic carrier [1] | ad 100 | ad 100 | ad 100 | ad 100 |

| | AF 17 | AF 18 | AF 19 | AF 20 |
|---|---|---|---|---|
| Oxidizing agent [2] | 0.5-20 | 1.0-18 | 1.2-16 | 1.5-15 |
| $C_8$-$C_{30}$ alcohol [3] | 0.50-7.0 | 0.50-6.5 | 1.0-6.0 | 1.0-5.0 |
| Anionic surfactant [4] | 0.10-7.0 | 0.10-5.5 | 0.10-4.0 | 0.20-3.5 |
| Non-ionic surfactant [5] | 0.10-4.0 | 0.12-3.0 | 0.15-2.5 | 0.20-2.0 |
| Cosmetic carrier [1] | ad 100 | ad 100 | ad 100 | ad 100 |

| | AF 21 | AF 22 | AF 23 | AF 24 |
|---|---|---|---|---|
| Oxidizing agent [2] | 0.5-20 | 1.0-18 | 1.2-16 | 1.5-15 |
| $C_8$-$C_{30}$ alcohol [3] | 0.50-7.0 | 0.50-6.5 | 1.0-6.0 | 1.0-5.0 |
| Anionic surfactant [4] | 0.10-7.0 | 0.10-5.5 | 0.10-4.0 | 0.20-3.5 |
| Non-ionic surfactant [5] | 0.10-4.0 | 0.12-3.0 | 0.15-2.5 | 0.20-2.0 |
| Cosmetic carrier [1] | ad 100 | ad 100 | ad 100 | ad 100 |

| | AF 21 | AF 22 | AF 23 | AF 24 |
|---|---|---|---|---|
| Oxidizing agent [2] | 0.5-20 | 1.0-18 | 1.2-16 | 1.5-15 |
| $C_8$-$C_{30}$ alcohol [3] | 0.50-7.0 | 0.50-6.5 | 1.0-6.0 | 1.0-5.0 |
| Anionic surfactant [4] | 0.10-7.0 | 0.10-5.5 | 0.10-4.0 | 0.20-3.5 |
| Non-ionic surfactant [5] | 0.10-4.0 | 0.12-3.0 | 0.15-2.5 | 0.20-2.0 |
| Acid | 0.1-3.0 | 0.5-2.5 | 0.8-2.0 | 0.9-1.5 |
| Cosmetic carrier [1] | ad 100 | ad 100 | ad 100 | ad 100 |

|  | AF 25 | AF 26 | AF 27 | AF 28 |
| --- | --- | --- | --- | --- |
| Oxidizing agent [2] | 0.5-20 | 1.0-18 | 1.2-16 | 1.5-15 |
| $C_8$-$C_{30}$ alcohol [3] | 0.50-7.0 | 0.50-6.5 | 1.0-6.0 | 1.0-5.0 |
| Anionic surfactant [4] | 0.10-7.0 | 0.10-5.5 | 0.10-4.0 | 0.20-3.5 |
| Non-ionic surfactant [5] | 0.10-4.0 | 0.12-3.0 | 0.15-2.5 | 0.20-2.0 |
| Complexing compound [6] | 0.10-1.0 | 0.10-0.80 | 0.10-0.60 | 0.10-0.50 |
| Acid [7] | 0.1-3.0 | 0.5-2.5 | 0.8-2.0 | 0.9-1.5 |
| Cosmetic carrier [1] | ad 100 | ad 100 | ad 100 | ad 100 |

[1] Aqueous or aqueous-alcoholic carrier

[2] Hydrogen peroxide, amount calculated on 100% hydrogen peroxide

[3] Mixture of linear $C_{14}$-$C_{18}$ alcohols, especially cetearyl alcohol

[4] Sodium salts of $C_{16}$-$C_{15}$ alkysulfates, especially sodium cetaryl sulfate

[5] Attachment products of 40 mol ethylene oxide to hydrogenated castor oil

[6] Ethylenediaminetetraacetic acid

[7] Mixture of disodium pyrophosphate and sodium benzoate

The previously described embodiments AF 1 to 28 are each packaged in packagung (VP) with the following layout of the multi-layer film (F) (from interior (in contact with the cosmetic composition (KM)) to exterior):

a) *Interior*-Layer (P1)-Layer (P2)-Barrier layer (BS)-*Exterior*, b) *Interior*-Layer (P1)-Barrier layer (BS)-Layer (P2)-*Exterior*, c) *Interior*-Layer (P2)-Layer (P1)-Barrier layer (BS)-*Exterior*, d) *Interior*-Layer (P2)-Barrier layer (BS)-Layer (P1)-*Exterior*, e) *Interior*-Barrier layer (BS)-Layer (P1)-Layer (P2)-*Exterior*, f) *Interior*-Barrier layer (BS)-Layer (P2)-Layer (P1)-*Exterior*, g) *Interior*-Layer (P1)-First adhesive layer (SK1)-Layer (P2)-Second adhesive layer (SK2)-Barrier layer (BS)-*Exterior*, h) *Interior*-Layer (P1)-Adhesive layer (SK1)-Layer (P2)-Barrier layer (BS)-*Exterior*, i) *Interior*-Layer (P1)-Layer (P2)-Second adhesive layer (SK2)-Barrier layer (BS)-*Exterior*, j) *Interior*-Barrier layer (BS)-First adhesive layer (SK1)-Layer (P1)-Second adhesive layer (SK2)-Layer (P2)-*Exterior*, k) *Interior*-Barrier layer (BS)-Adhesive layer (SK)-Layer (P1)-Layer (P2)-*Exterior*, l) *Interior*-Barrier layer (BS)-Layer (S1)-Adhesive layer (SK)-Layer (P2)-*Exterior*, m) *Interior*-Layer (P1)-First adhesive layer (SK1)-Barrier layer (BS)-Second adhesive layer (SK2)-Layer (P2)-*Exterior*, n) *Interior*-Layer (P1)-Adhesive layer (SK)-Barrier layer (BS)-Layer (P2)-*Exterior*, o) *Interior*-Layer (P1)-Barrier Layer (BS)-Adhesive layer (SK)-Layer (P2)-*Exterior*.

The products obtained in this way have a high storage stability and a water loss during storage that is within an acceptable range. No swelling or delamination of the packaging (VP) during storage of these cosmetic products was observed.

The product as contemplated herein is used for the purpose of oxidative color change. For this purpose, the composition (KM) packaged in the packaging (VP), which is the oxidizing agent composition, is mixed with at least one further composition (B) to produce the ready-to-use color changing agent. To prevent incompatibilities or premature reaction, the compositions (KM) and (B) are packaged separately.

A particularly preferred product as contemplated herein comprises a composition (B) separately prepared from composition (KM), wherein composition (B) contains at least one compound selected from oxidative colorant precursor, direct dyes, alkalizing agents and mixtures thereof. Preferred products of the present disclosure additionally comprise at least one second cosmetic composition (KM2) which contains at least one compound selected from oxidative colorant precursor, direct dyes, alkalizing agents and mixtures thereof and which is packaged separately from the cosmetic composition (KM).

If oxidative coloration is desired, composition (B) contains at least one oxidative colorant precursor. Oxidative colorant precursors may be divided into developers and couplers, whereby the developers are usually used in the form of their physiologically compatible salts (e.g. in the form of their hydrochlorides, hydrobromides, hydrogen sulfates or sulfates) due to their greater sensitivity to oxygen. Coupler components alone do not form a significant coloration in the course of oxidative coloration, but always require the presence of developer components. Preferably such agents contain at least one oxidative colorant precursor of the developer type and at least one oxidative colorant precursor of the coupler type. Particularly suitable oxidative colorant precursors of the developer type are selected from at least one compound from the group formed by p-phenylenediamine, p-toluenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine N,N'-bis-(2-hydroxyethyl)-N,N'-bis-(4-aminophenyl)-1,3-di-amino-propane-2-ol, bis-(2-hydroxy-5-aminophenyl) methane, 1,3-bis-(2,5-diaminophenoxy)propane-2-ol, N,N'-bis-(4-aminophenyl)-1,4-diazacycloheptane, 1,10-bis-(2,5-diaminophenyl)-1,4,7,10-tetraoxadecane p-aminophenol, 4-amino-3-methylphenol, 4-amino-2-aminomethylphenol, 4-amino-2-(1,2-dihydroxyethyl)phenol, 4-amino-2-(diethylaminomethyl)phenol 4,5-diamino-1-(2-hydroxyethyl)pyrazole, 2,4,5,6-tetraamino-pyrimidine, 4-hydroxy-2,5,6-triaminopyrimidine, 2-hydroxy-4,5,6-triamino-pyrimidine, 2,3-diamino-6,7-dihydro-1H,5H-pyrazolo[1,2-a]pyrazol-1-on and their physiologically compatible salts.

Particularly suitable oxidative colorant precursors of the coupler type are selected from the group formed by 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylene-diamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino}-2-methoxy-5-methylphenyl]amino) ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxy-ethoxy)-5-methylphenylamine, 1-amino-3-bis-(2-hydroxyethyl) aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxy-naphthalene, 2,7-dihydroxynaphthalene, 1,7-dihydroxynaphthalene, 1,8-dihydroxy-naphthalene, 4-hydroxyindole, 6-hydroxyindole, 7-hydroxyindole, 4-hydroxyindoline, 6-hydroxyindoline, 7-hydroxyindoline or mixtures of these compounds or their physiologically acceptable salts.

In addition, the composition (B) may also contain one or more direct dyes. Suitable non-ionic direct dyes may be selected from the group HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, 1,4-diamino-2-nitrobenzene, 2-amino-4-nitrophenol, 1,4-bis(2-hydroxyethyl)-amino-2-nitrobenzene, 3-nitro-4-(2-hydroxyethyl)aminophenol, 2-(2-hydroxyethyl)amino-4,6-dinitro-phenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 4-[(3-hydroxypropyl)amino]-3-nitrophenol, 4-nitro-o-phenylenediamine, 6-nitro-1,2,3,4-tetrahydroquinone, 2-hydroxy-1,4-naphthoquinone, picramine acid and its salts, 2-amino-6-chloro-4-nitrophenol, 4-ethylamino-3-nitrobenzoic acid and 2-chloro-6-ethylamino-4-nitrophenol.

Suitable anionic direct dyes may be selected from the group including Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, Bromophenol Blue and Tetrabromophenol Blue.

Suitable cationic direct dyes are cationic triphenylmethane dyes, such as Basic Blue 7, Basic Blue 26, Basic Violet 2 and Basic Violet 14, aromatic systems substituted with a quaternary nitrogen group, such as Basic Yellow 57, Basic Red 76, Basic Blue 99, Basic Brown 16 and Basic Brown 17, cationic anthraquinone dyes, such as HC Blue 16 (Bluequat B), and direct dyes containing a heterocycle containing at least one quaternary nitrogen atom, in particular Basic Yellow 87, Basic Orange 31 and Basic Red 51. The cationic direct dyes marketed under the trademark Arianor are also suitable cationic direct dyes as contemplated herein.

Dyeing processes on keratinous fibers are usually carried out in an alkaline environment. In order to protect the keratinous fibers and also the skin as much as possible, however, the adjustment of a too high pH value is not desirable. Therefore, it is preferable if the pH value of agent (B) is between about 7 and about 11, especially between about 8 and about 10.5. For the purposes of the present disclosure, the pH values are pH values measured at a temperature of 22° C.

Composition (B) may contain at least one alkalizing agent. The alkalizing agents usable for adjusting the preferred pH value as contemplated herein may be selected from the group formed by ammonia, alkanolamines, basic amino acids, and inorganic alkalizing agents such as (earth) alkali metal hydroxides, (earth) alkali metal metasilicates, (earth) alkali metal phosphates and (earth) alkali metal hydrogen phosphates. Preferred inorganic alkalizing agents are magnesium carbonate, sodium hydroxide, potassium hydroxide, sodium silicate and sodium metasilicate. Organic alkalizing agents which can be used as contemplated herein are preferably selected from monoethanolamine, 2-amino-2-methyl-propanol and triethanolamine. The basic amino acids usable as alkalizing agents as contemplated herein are preferably selected from the group formed from arginine, lysine, ornithine and histidine, especially preferably arginine. However, in the course of the investigations into the present disclosure, it was found that further agents preferred as contemplated herein are exemplified by the fact that they additionally contain an organic alkalizing agent. An embodiment of the first agent as contemplated herein additionally contains at least one alkalizing agent selected from the group formed by ammonia, alkanolamines and basic amino acids, in particular ammonia, monoethanolamine and arginine or its compatible salts.

Composition (B) may further contain additional active ingredients, auxiliary substances and additives. For example, one or more fat components from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons may be included.

Preferably, a surface-active substance may be added to composition (B), whereby such surface-active substances are referred to as surfactants or emulsifiers, depending on the area of application: they are preferably selected from anionic, zwitterionic, amphoteric and non-ionic surfactants and emulsifiers.

Composition (B) preferably contains at least one anionic surfactant. Preferred anionic surfactants are fatty acides, alkyl sulfates, alkyl ether sulfates and ether carbon acids with 10 to 20 carbon atoms in the alkyl group and up to 16 glycol ether groups in the molecule.

Furthermore, composition (B) may additionally contain at least one zwitterionic surfactant. Preferred zwitterionic surfactants are betaines, N-alkyl-N,N-dimethylammoniumglycinate, N-acyl-aminopropyl-N,N-dimethylammoniumglycinate, and 2-alkyl-3-carboxymethyl-3-hydroxyethylimidazolines. A preferred zwitterionic surfactant is known under the INCI designation Cocamidopropyl Betaine.

Furthermore, it may be intended that the composition (B) contains at least one amphoteric surfactant. Preferred amphoteric surfactants are N-alkylglycine, N-alkylpropionic acid, N-alkyl-aminobutter acid, N-alkyliminodipropionic acid, N-hydroxyethyl-N-alkylamidopropylglycine, N-alkyltaurine, N-alkylsarcosine, 2-alkylaminopropionic acid and alkylaminoacetic acid. Particularly preferred amphoteric surfactants are N-coconut alkylaminopropionate, as coconut acylaminoethylamino propionate and $C_{12}$-$C_{15}$ acyl sarcosine.

Furthermore, it has proven to be advantageous if the composition (B) contains further, non-ionic surface-active substances. Preferred non-ionic surfactants are alkylpolyglycoside and alkylene oxide plant products on fatty alcohols and fatty acids with 2 to 30 moles of ethylene oxide per mole of fatty alcohol or fatty acid. Compositions with outstanding properties are also obtained if they contain fatty acid esters of ethoxylated glycerol as non-ionic surfactants.

The non-ionic, zwitterionic or amphoteric surfactants are used in proportions of from about 0.1 to about 45% by weight, preferably from about 1 to about 30% by weight and particularly preferably from about 1 to about 15% by weight, based on the total weight of the composition (B).

Composition (B) may also contain at least one thickening agent. There are no restrictions in principle with regard to these thickening agents. Both organic and purely inorganic thickening agents may be used. Suitable thickening agents are anionic, synthetic polymers, cationic, synthetic polymers, naturally occurring thickening agents such as non-ionic guar gums, scleroglucan gums or xanthane gums, gum arabicum, ghatti gum, karaya gum, tragacanth gum, carrageenan gum, agar-agar, carob bean gum, pectins, alginates, starch fractions and derivatives such as amylose, amylopectin and dextrine, as well as cellulose derivatives such as methyl cellulose, carboxyalkyl celluloses and hydroxyalkyl celluloses, non-ionic, fully synthetic polymers such as polyvinyl alcohol or polyvinyl pyrrolidinone as well as inorganic thickening agents, in particular phyllosilicates such as bentonite, especially smectites such as montmorillonite or hectorite.

Furthermore, composition (B) may contain other active ingredients, auxiliary substances and additives, such as non-ionic polymers such as vinyl pyrrolidine/vinyl acrylate copolymers, polyvinylpyrrolidinone, vinylpyrrolidine/vinyl acetate copolymers, polyethylene glycols and poly-siloxanes; additional silicones such as volatile or non-volatile, straight-chain, branched or cyclic, crosslinked or non-crosslinked polyalkylsiloxanes (such as dimethicones or cyclomethicones), polyarylsiloxanes and/or polyalkylarylsiloxanes, in particular polysiloxanes with organo-functional groups, such as substituted or unsubstituted amines (amodimethicones), carboxyl, alkoxy and/or hydroxyl groups (dimethicone copolyols), linear polysiloxane(A)-polyoxyalkylene (B) block copolymers, grafted silicone polymers; cationic polymers such as quaternized cellulose ethers, polysiloxanes with quaternary groups, dimethyldiallylammonium chloride polymers, acrylamidedimethyldiallylammonium chloride copolymers, dimethylaminoethyl methacrylate-vinylate vinyl pyrrolidinone copolymers quaternized with diethyl sulfate, vinyl pyrrolidinone-imidazolium methochloride copolymers and quaternized polyvinyl alcohol; zwitterionic and amphoteric polymers; anionic polymers such as, for example, polyacrylacids or cross-linked polyacrylics; structurants such as glucose, maleic acid and lactic acid, hair-conditioning compounds such as phospholipids, for example lecithin and cephalins; perfume oils, dimethyl isosorbide and cyclodextrins; fiber structure-improving active substances, in particular mono-, di- and oligo-saccharides such as glucose, galactose, fructose, fructose and lactose; dyes for colouring the composition; anti-dandruff active substances such as piroctone olamines, zinc omadine and climbazole; amino acids and oligopeptides; animal and/or vegetable-based protein hydrolysates, as well as in the form of their fatty acid condensation products or optionally anionically or cationically modified derivatives; fatty substances and vegetable oils; sunscreens and UV blockers; active ingredients such as panthenol, panthenic acid, pantolactone, allantoin, pyrrolidinone-carbon acid and its salts, and bisabolol; polyphenols, in particular hydroxyzine acids, 6,7-dihydroxycoumarins, hydroxybenzoic acids, catechins, tannins, leucoanthocyanidins, anthocyanidins, flavanones, flavones and flavonols; ceramides or pseudoceramides; vitamins, provitamins and vitamin precursors; plant extracts; fats and waxes such as fatty alcohols, beeswax, montan wax and paraffins; swelling and penetrating agents such as glycerine, propylene glycol monoethyl ether, carbonates, hydrogen carbonates, guanidines, ureas as well as primary, secondary and tertiary phosphates; anti-caking agents such as latex, styrene/PVP and styrene/acrylamide copolymers; pearlescent agents such as ethylene glycol mono- and distearate as well as PEG-3 distearate and pigments.

The selection of these additional substances will be made by the expert according to the desired properties of the composition (B) as well as the product as contemplated herein. With regard to further optional components and the quantities of these components used, explicit reference is made to the relevant handbooks known to the expert. The additional active ingredients and auxiliary substances are preferably used in the composition (B) in quantities of from about 0.0001 to about 25% by weight each, in particular from about 0.0005 to about 15% by weight, in each case based on the total weight of the composition (B).

The following examples explain the present disclosure without limiting it:

EXAMPLES

A 100 nm thick layer of aluminum was vapor-deposited onto a film layer of biaxially oriented polypropylene with a thickness of 12 μm (micrometres). The aluminum layer was then painted over with approx. 3 g/m$^2$ of ORMOCER polymer and cured. A 70 μm (micrometer) thick layer of polyethylene was then applied to the ORMOCER layer. A packaging (VP) was produced from the film. The film is also provided with a PET layer 20 μm thick.

The following cosmetic compositions (KM) were used (all figures in % by weight).

| Ingredients | KM |
| --- | --- |
| Potassium hydroxide (50%)) | 0.15 |
| Sodium benzoate | 0.04 |
| Disodium pyrophosphate | 0.1 |
| Dipicolin acid | 0.03 |
| 1-hydroxyethan-1,1-diphosphonacid (60% ig) | 0.31 |
| Oxidizing agent [1] | 11.9 |
| $C_8$-$C_{30}$ alcohol [2] | 1.7 |
| Anionic surfactant [3] | 0.18 |
| Non-ionic surfactant [4] | 0.33 |
| Water | ad 100 |

[1] Preferably hydrogen peroxide, calculated to 100% $H_2O_2$
[2] Preferably a mixture of linear $C_{14}$-$C_{18}$ alcohols, especially cetearyl alcohol
[3] Preferably a sodium salt of $C_{16}$-$C_{18}$ alkysulfates, especially sodium cetaryl sulfate
[4] Preferably attachment products of 40 mol ethylene oxide to hydrogenated castor oil, particularly PEG-40 hydrogenated Castor Oil oder Emulgin RO 40

Furthermore, the following cosmetic compositions (KM) were used (all figures in % by weight).

| Ingredients | KM |
| --- | --- |
| Potassium hydroxide (50%)) | 0.24 |
| Sodium benzoate | 0.04 |
| Disodium pyrophosphate | 0.1 |
| Dipicolin acid | 0.1 |
| 1-hydroxyethan-1,1-diphosphonacid (60% ig) | 0.31 |
| Oxidizing agent [1] | 11.9 |
| $C_8$-$C_{30}$ alcohol [2] | 1.7 |
| Anionic surfactant [3] | 0.18 |
| Non-ionic surfactant [4] | 0.33 |
| Water | ad 100 |

[1] Preferably hydrogen peroxide, calculated to 100% $H_2O_2$
[2] Preferably a mixture of linear $C_{14}$-$C_{18}$ alcohols, especially cetearyl alcohol
[3] Preferably a sodium salt of $C_{16}$-$C_{18}$ alkysulfates, especially sodium cetaryl sulfate
[4] Preferably attachment products of 40 mol ethylene oxide to hydrogenated castor oil, particularly PEG-40 hydrogenated Castor Oil oder Emulgin RO 40

The cosmetic composition KM was filled into the previously described packaging (VP). Then the packagings were stored at 40° C. for 24 weeks. The packagings were not inflated or delaminated.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic product for modifying the natural color of keratinous fibers comprising
   (i) a packaging comprising a multi-layer film, wherein the multi-layer film comprises a first polymer layer, a second polymer layer and a barrier layer, and
   (ii) a cosmetic composition packaged in the packaging and comprising:
      a) an oxidizing compound,
      b) a $C_8$-$C_{30}$ alcohol,
      c) an anionic surfactant and
      d) a non-ionic surfactant
      wherein the first polymer layer is formed of polyethylene terephthalate or polyethylene naphthalate; the second polymer layer is formed of a polyolefin; and the barrier layer is formed of metallized oriented polypropylene.

2. The cosmetic product according to claim 1, wherein the first polymer layer has a layer thickness of from about 4 μm to about 50 μm; the second polymer layer has a layer thickness of from about 20 μm to about 150 μm; and the layer thickness of the barrier layer is from about 4 μm to about 20 μm.

3. The cosmetic product according to claim 1, wherein the multi-layer film has an oxygen transmission rate at about 23° C. and about 50% relative humidity of from about 0.1 to about 5 cc/m$^2$/d/bar, and a water vapor permeability at about 38° C. and about 100% relative humidity of from about 0.1 to about 5 g/m$^2$d.

4. The cosmetic product according to claim 1, wherein the multi-layer film has an adhesive strength of from about 0.1 to about 10 N/15 mm; and/or wherein the multi-layer film has a seal strength of from about 10 to about 40 N/15 mm under the conditions of about 150° C., about 2.54 cm (1") and about 4 kg/cm$^2$.

5. The cosmetic product according to claim 1, wherein the multi-layer film comprises the barrier layer between the first polymer layer and the second polymer layer; and wherein the first polymer layer forms an outer layer of the packaging.

6. The cosmetic product according to claim 1, wherein the cosmetic composition has a pH value (measured at about 20° C.) of between about pH 1.5 and about pH 5.0.

7. The cosmetic product according to claim 1, wherein the cosmetic composition comprises the oxidizing compound in a total amount of from about 0.5 to about 20% by weight, relative to a total weight of the cosmetic composition.

8. The cosmetic product according to claim 1, wherein the cosmetic composition comprises the $C_8$-$C_{30}$ alcohol in a total amount of from about 0.5 to about 8% by weight, based on a total weight of the cosmetic composition.

9. The cosmetic product according to claim 1, wherein the cosmetic composition comprises the non-ionic surfactant in a total amount of from about 0.1 to about 4% by weight, relative to a total weight of the cosmetic composition (KM).

10. The cosmetic product according to claim 1, wherein the cosmetic composition comprises the anionic surfactant in a total amount of from about 0.1 to about 7% by weight, relative to a total weight of the cosmetic composition (KM).

11. The cosmetic product according to claim 1, wherein the cosmetic composition comprises the oxidizing compound in a total amount of from about 1.0 to about 18% by weight, based on a total weight of the cosmetic composition.

12. The cosmetic product according to claim 1, wherein the cosmetic composition comprises the oxidizing compound in a total amount of from about 1.2 to about 16% by weight, based on a total weight of the cosmetic composition.

13. The cosmetic product according to claim 1, wherein the cosmetic composition comprises the oxidizing compound in a total amount of from about 1.5 to about 15% by weight, based on a total weight of the cosmetic composition, and wherein the oxidizing compound comprises hydrogen peroxide.

14. The cosmetic product according to claim 1, wherein the cosmetic composition comprises the $C_8$-$C_{30}$ alcohol in a total amount of from about 1.0 to about 6% by weight, based on a total weight of the cosmetic composition.

15. The cosmetic product according to claim 1, wherein the cosmetic composition comprises the $C_8$-$C_{30}$ alcohol in a total amount of from about 1.5 to about 4% by weight, based on a total weight of the cosmetic composition, and wherein the $C_8$-$C_{30}$ alcohol is a mixture of linear $C_{14}$-$C_{18}$ alcohols.

16. The cosmetic product according to claim 1, wherein the first polymer layer has a layer thickness of from about 6 μm to about 20 μm; the second polymer layer has a layer thickness of from about 40 μm to about 90 μm; and the layer thickness of the barrier layer is from about 6 μm to about 15 μm.

17. The cosmetic product according to claim 1, wherein the cosmetic composition comprises the non-ionic surfactant in a total amount of from about 0.15 to about 2.5% by weight, based on a total weight of the cosmetic composition.

18. The cosmetic product according to claim 1, wherein the cosmetic composition comprises the non-ionic surfactant in a total amount of from about 0.2 to about 2% by weight, based on a total weight of the cosmetic composition, and wherein the non-ionic surfactant comprises attachment products of 40 mols of ethylene oxide to hydrogenated castor oil.

19. The cosmetic product according to claim 1, wherein the cosmetic composition comprises the anionic surfactant in a total amount of from about 0.10 to about 4.0% by weight, based on a total weight of the cosmetic composition.

20. The cosmetic product according to claim 1, wherein the cosmetic composition comprises anionic surfactant in a total amount of from about 0.10 to about 3.5% by weight, based on a total weight of the cosmetic composition, and wherein the anionic surfactant comprises sodium salts of $C_{14}$-$C_{18}$ alkyl sulfates.

* * * * *